United States Patent
Sage, Jr.

(10) Patent No.: US 6,582,393 B2
(45) Date of Patent: Jun. 24, 2003

(54) COMPENSATING DRUG DELIVERY SYSTEM

(75) Inventor: Burton H. Sage, Jr., Vista, CA (US)

(73) Assignee: Therafuse, Inc., Vista, CA (US)

( * ) Notice: Subject to any disclaimer, the term of this patent is extended or adjusted under 35 U.S.C. 154(b) by 0 days.

(21) Appl. No.: 09/867,003

(22) Filed: May 29, 2001

(65) Prior Publication Data

US 2003/0018304 A1 Jan. 23, 2003

(51) Int. Cl.⁷ .............................................. A61M 31/00
(52) U.S. Cl. ....................................................... 604/65
(58) Field of Search ............................. 604/48, 65–67, 604/181, 93.01, 118, 121, 131, 30, 31, 113, 114, 246, 250

(56) References Cited

U.S. PATENT DOCUMENTS 5,211,626 A * 5/1993 Frank et al. .................. 604/65
5,575,770 A * 11/1996 Melsky et al. ................ 604/93
5,848,990 A * 12/1998 Cirelli et al. ................ 604/136
6,162,202 A * 12/2000 Sicurelli et al. ............ 604/272

FOREIGN PATENT DOCUMENTS

EP 1 177 802 A1 6/2002

* cited by examiner

*Primary Examiner*—Michael J. Hayes
*Assistant Examiner*—Ann Y. Lam
(74) *Attorney, Agent, or Firm*—Foley & Lardner

(57) ABSTRACT

A compensating drug delivery system for delivery of medicaments to animals is described. A drug-containing reservoir is connected to a needle array through a flow tube. Medicament delivery to the animal through this flow tube is regulated by the combined action of a metering means and a valving means, and inaccuracies in delivery rate are compensated. The metering means and the valving means are microprocessor controlled to insure that the medication administered is according to a pre-established protocol.

23 Claims, 2 Drawing Sheets

COMPENSATING DRUG DELIVERY SYSTEM

BACKGROUND OF THE INVENTION

A. Field of the Invention

The present invention relates to the general field of medicinal therapy and the specific field of drug delivery methods for administering medicaments to accomplish a desired therapy. More particularly, the present invention relates to a dose metering drug delivery system with automatic compensation of variations in device parameters for accurate delivery of selected pharmaceutical agents according to a predetermined schedule.

B. Related Art

Drug delivery systems with pressurized fluid reservoirs for parenteral administration of selected pharmaceutical agents are not new. In principle, there is no simpler drug infusion system than fluid in a pressurized bag connected to a tube to deliver the fluid into the body through a needle. It is not surpising, then, that a number of such drug delivery systems have been patented, including U.S. Pat. No. 3,469,578 issued to Bierman and U.S. Pat. No. 4,318,400 issued to Perry. As elegant and simple as these systems are, it was quickly appreciated that the ability of these devices to accurately and reproducibly deliver the contained fluid was limited. Flow through the tube is dependent on several parameters, including the length of the flow tube, the inside diameter of the flow tube, the pressure in the reservoir, and the viscosity of the fluid being delivered, which in turn is dependent on the temperature of the fluid.

In early systems with elastomeric drug reservoirs, the pressure variation proved to be the biggest problem since it would start out at a maximum value and then decrease to almost nothing when the last drops of fluid were delivered. Hence improvements were sought to keep the pressure constant, including the improvements described in U.S. Pat. No. 4,447,224, issued to Idriss, that teaches monitoring the pressure difference between the ends of a flow resistor, and adjusting the flow resistor such that the pressure difference is constant. Sealfon in U.S. Pat. Nos. 4,741,736 and 4,447,232, and Bryant, et.al., in U.S. Pat. No. 5,248,300 teach the use of various constant force springs as an improvement to reduce pressure variation as the reservoir empties. Sampson in U.S. Pat. No. 5,061,242 teaches the use of a fluid in contact with its own vapor to achieve a constant pressure for a medicament solution. And McPhee in U.S. Pat. No. 5,665,070 teaches the use of a magnetic field to urge magnetic plates together to achieve constant force on a fluid.

The passive variety of systems does a good job of reducing the pressure variation, but they are also only single flow rate devices. For many medicaments there is a need to vary the rate of delivery of the drug over time, and to program the device such that the desired delivery schedule is achieved. This invariably complicates the system, making it more expensive. In efforts to keep the cost down, two component systems were designed wherein the expensive programmable and controlling unit could be reused, and the inexpensive drug containing reservoir could be disposed. Because of the need to maintain sterility in the parts of the system in contact with the drug fluid, the disposable component also included a flow tube and a body entry component such as a needle. This need for programming, and the requirement to minimize overall cost proved to be the undoing of the passive constant pressure systems. None are known to be marketed today.

Because of the need for time variations in delivery rate and the need for improved accuracy, two classes of drug delivery pumps have emerged as preferred—the syringe pump and the peristaltic pump. Both achieve accuracy through positive displacement of the volume to be delivered, taking pressure and viscosity out of the equation. The syringe pump also takes the inside diameter of the flow tube out of the equation. Both the syringe pump and the peristaltic pump are in common use today.

Perhaps the best known of these pumps is the MiniMed insulin delivery product (See www.minimed.com). It is a pager-sized device typically worn on the belt. The drug is delivered down a long flexible tube and enters the body through a relatively large bore catheter placed in the skin by the patient. Similar but larger devices known as drug delivery pumps are used in hospitals. Perhaps best known of these pumps are those used to administer narcotics for Patient Controlled Analgesia such as the pump manufactured by Abbott Laboratories. This and similar pumps are also used for intravenous infusion of additional drugs such as oncologics and antibiotics.

While the MiniMed product is highly regarded for providing improved therapy to diabetics by automatically infusing insulin according to a physician-determined regimen specific for every patient, the product suffers from several deficiencies. First, the skin-traversing catheter must be placed using a large-bore metal needle. The placement of this needle must be done by the patient himself or a caregiver. The placement of this needle is quite painful, and must be done every third day. Second, the liquid drug is administered by counting the revolutions of a motor that pushes the barrel in a syringe. As such, the actual quantity administered is unknown, since it is calculated from expected device properties such as the expected cross-sectional area of the syringe barrel. Since the actual diameter varies from syringe to syringe, and this syringe is frequently changed, the actual delivery varies over time. And since differences in delivery are related to the cross-sectional area of the barrel, small differences in barrel diameter are magnified. Third, flow tubes such as the one used in the MiniMed device are subject to becoming clogged. When the tube is clogged, no insulin is administered, a life-threatening situation for a diabetic. Although the product is sold with a clog alarm, experience with the product shows that delays in warning of clogs can be as high as twelve hours. Diabetics can become comatose in less time than this if they don't get their insulin. Fourth, the product is relatively large. Diabetics are very conscious of the fact that they are not normal, and hiding this relatively large product is not easy. Most men wear this product on their belts like a pager, and most women either wear loose fitting clothes to hide the product or wear it in a specially designed bra. Fifth, the product is very expensive. The MiniMed pump, which lasts 3–5 years, costs many thousands of dollars, and the three-day tubing set costs between $15 and $20. The annual cost per diabetic using this product is between $2,800 and $3,500, with most of the cost being the cost of the replaceable tubing set. Sixth, the MiniMed product requires the use of electrical energy to move the fluid from the drug reservoir into the body. This method requires frequent changing of batteries, further adding to the overall cost of use of the product. Therefore, while the MiniMed product has achieved its goal of continuous programmable administration of insulin, the actual embodiment leaves much to be desired. While the delivery of insulin is relatively accurate, the product is not user-friendly product, requiring a highly motivated user, and it is expensive. These facts are the primary reason only about one diabetic in a hundred actually uses this product.

In recent years there have been a number of attempts to improve on the MiniMed product. Brown, in U.S. Pat. No. 4,741,736 teaches the use of an optical system to monitor the position of a roller that is used to press a fluid reservoir. If the roller fails to move the proper distance in the proper time, then delivery of the fluid is not as desired. A flow restrictor is then adjusted to achieve the correct fluid delivery rate. However, this system is slow, and can only make adjustments to compensate future delivery based on a measured earlier result. The implantable Shiley Infusaid™, U.S. Pat. No. 4,447,224 improves on the body image of the MiniMed product by being surgically implanted. But the expense of using the product was even greater. Elan (Gross, U.S. Pat. No. 5,527,288) is developing a wearable product that is smaller than the MiniMed product and does not require the long tubing set. While this is an improvement, the method of pumping, which requires turning water into gas through electrolysis, results in a very low compliance system that delivers liquids with even less accuracy than the MiniMed product. The delivery is slow in starting, and even slower in stopping. The Elan system also requires that a large bore metal needle remain in the body during all times the system would be worn. Finally, the entire system, including the pumping mechanism, is disposable, making the system very expensive. Another, similar, disposable system has been patented by Hoff-man La-Roche (Cirelli, U.S. Pat. No. 4,886,499). It is an improvement over the Elan system in that delivery is by the positive displacement method. But it also is entirely disposable, making it expensive. Science, Inc. (Kriesel, U.S. Pat. No. 5,016,047) has developed a novel method of using an elastomeric pressurized reservoir for delivery of therapeutic liquids. However, the system as described is completely passive, with no control over the flow of the liquids. Flow is entirely dependent upon the physical parameters of the system—the length and average cross-sectional area of the path from reservoir to the body, the temperature of the environment, the viscosity of the liquid being delivered, and the actual pressure in the reservoir. Further, there is no method of changing the flow rate from the nominal design, making programmable delivery impossible. While this design is particularly ingenious through its use of geometry, it is also particularly impractical because of the very tight tolerances required during the manufacturing process to insure reproducible delivery.

A novel method of insuring accurate flow rates in a liquid system is described by Jerman (U.S. Pat. No. 5,533,412). Using a method taught as thermal time of flight, the motion of a small heated volume of fluid down a flow path is measured. As described in this patent, pressure variations are easily compensated. However, for use as a wearable drug delivery system, this system is impractical since the entire device is etched from silicon to insure highly accurate dimensions. Hence the entire device must be discarded after each use, which is expensive, or the liquid flow path of the system must be opened to insert this flow meter, providing an opportunity for contamination.

It can thus be seen that there continues to be a need for a drug delivery system that compensates for system variables, especially in an economical reusable controller, disposable drug reservoir configuration and in a much more convenient and comfortable package.

The primary objective of this invention is to provide a device for more accurate, comfortable, convenient, and cost-effective programmable delivery of therapeutic liquids.

A second objective of this invention is to provide safer administration of therapeutic liquids through real-time measurement of liquid flow to provide real-time compensation for system variables.

Another objective of this invention is to provide a system for programmable delivery of therapeutic liquids that does not require electrical energy to move the liquid, thereby reducing the need for frequent battery replacement and providing a smaller system at lower overall cost.

A further objective of this invention is to provide an insulin delivery system that is attractive and beneficial to, and cost effective for the great majority of diabetics.

A further objective of this invention is to provide a small, wearable delivery system for narcotic analgesics for the management of moderate to severe pain.

A still further objective of this invention is to provide a cost-effective dosage form for other drugs that require accurate delivery according to either a predetermined protocol or a patient specific protocol.

BRIEF SUMMARY OF THE INVENTION

These objectives are realized through the unique combination of components of this invention. In a preferred embodiment, a small short flexible tube connects a thin mechanically pressurized drug reservoir and an array of microneedles. This embodiment is shown schematically in FIG. 1. An electrically actuated tube-pinching means is used to regulate liquid flow through this tube by intermittently pinching the tube to stop flow or not pinching the tube so that liquid may flow. A heating element is placed between the drug reservoir and the pinching mechanism to heat the small increment of fluid within it. A heat sensor is placed between the pinching mechanism and the array of microneedles to sense the presence of this increment of fluid when it flows by.

In operation, at the beginning of a cycle, the system first pinches the tube so that there is no liquid flow. The heater is then actuated to heat a small segment of the fluid stream. The pinching mechanism is then opened so that the liquid flows through the tube. This moves the heated segment of liquid past the heat sensor. The time that it takes the heated segment to reach the heat sensor is recorded. A microprocessor then compares this measured time to an expected time interval based on the geometry of the system and determines if the flow rate is too low or too high. It then calculates the amount of time the pinching mechanism needs to continue to remain open during the cycle to achieve the desired drug delivery rate, thereby compensating for the unique variances from nominal in the actual device. Once this time has passed, the pinching mechanism repinches the tube, and drug delivery stops for the remainder of the cycle.

This process is repeated, resulting in a series of cycles during which the pinching mechanism is opened, a flow time is measured and compared to an expected time, a fraction of a cycle time is calculated such that the desired delivery is achieved, and the pinching mechanism is closed, stopping flow.

The desired amount of liquid delivered by this method can be achieved by adjusting the fraction of the cycle the pinching mechanism allows the liquid to flow. Thus there is a maximum delivery rate (the pinch valve is open almost all the time) and a minimum delivery rate (dictated by the volume of fluid between the heater and the heat sensor). Thus it can be seen that a continuous range of accurate drug delivery rates can be obtained by measuring the time required for an increment of fluid to flow between the heating element and the heat sensor and adjusting the fraction of a drug delivery cycle that flow is permitted.

DETAILED DESCRIPTION OF THE INVENTION

Figure 1:
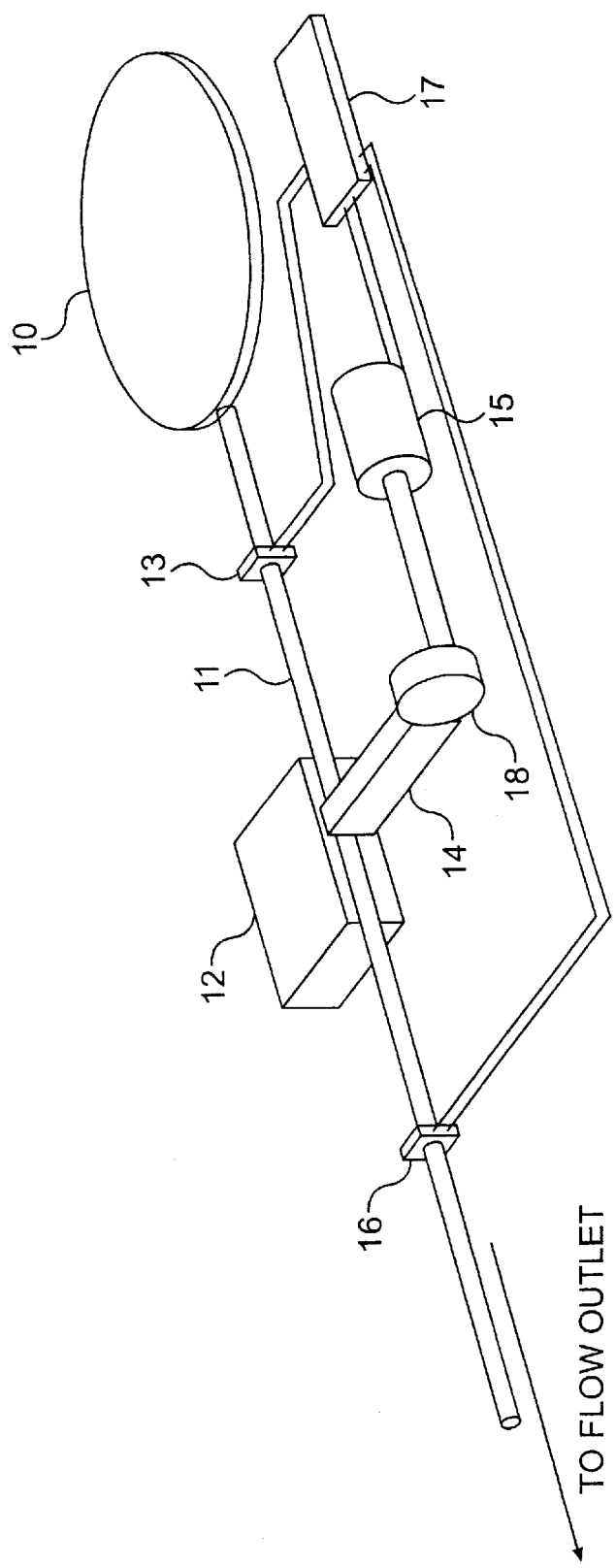
FIG. 1 is a block diagram showing the components of a preferred embodiment of the invention that uses the "thermal time-of-flight" method of compensating for variations in the components and parameters of a drug delivery system.

Reference is made to FIG. 1, which shows a preferred embodiment of the invention. The drug to be delivered to the animal has been stored in reservoir 10. Reservoir 10 is a pre-pressurizing container that stores the drug at a desired mechanical pressure during the filling process. Typically, reservoir 10 has an inner liner for contacting the stored drug in a drug stability-preserving manner. The inner liner may be made from polymers acceptable for being in contact with pharmaceutical solutions for long periods of time or other materials having the required properties as are known in the art. The inner liner is typically in physical contact with an outer layer used as the structural element of reservoir 10. The outer layer may be made from metals such as steel, aluminum, or similar metal capable of preserving an internal pressure for several years. Alternatively, the structural layer may be made from a variety of polymers such as polyolefins including specifically particle filled polymers that are capable of storing the drug at the desired mechanical pressure for several years.

At time of use, flow tube 11 is connected to reservoir 10 in such a manner that the drug fluid in reservoir 10 may flow through flow tube 11 to the flow outlet (microneedle array) and into the animal to be treated. The microneedles (not shown) may be made of stainless steel as is conventional, or may be made of polysilicon or silicon, or may be preferably made of shape memory allow because of the very high elastic limit of these materials. Flow tube 11 is made of a flexible, drug compatible polymer such as Vialon™ that may be alternately pinched shut using pinch bar 14 and pinch stop 12 to stop the flow of the drug, or may be reopened to flow by withdrawing pinch bar 14 from pinch stop 12.

Figure 2:
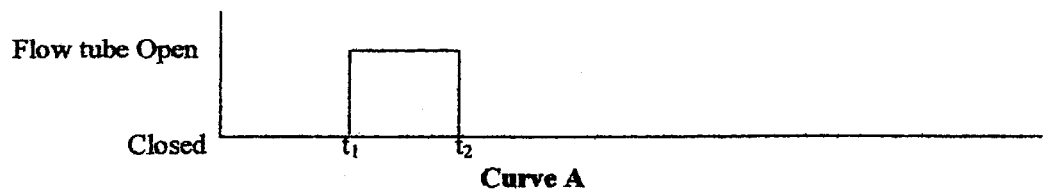
FIG. 2 is a timing diagram to demonstrate the capability of the invention to deliver the selected drug at different delivery rates through a continuous series of cycles where flow is allowed only a portion of the cycle. This process is commonly known as pulse-width modulation.
Figure 2:
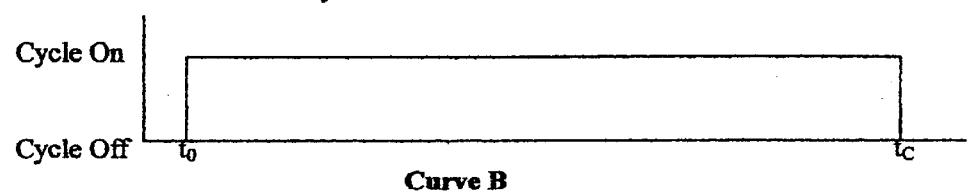
Figure 2:
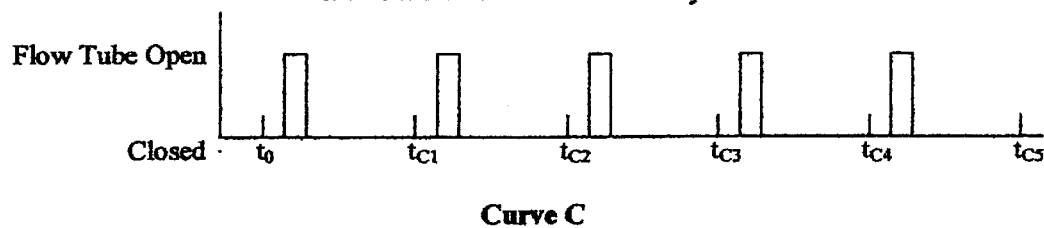

In order to regulate the rate of delivery of the drug into an animal such that the proper liquid volume, and hence the proper quantity of drug substance, is delivered at the proper time over the period when the drug delivery system is used, flow of the drug liquid down flow tube 11 must be regulated. This is accomplished with a calculated time sequence of pinching and unpinching of flow tube 11 using pinch bar 14 and pinch stop 12, thereby regulating the flow of the drug liquid through flow tube 11 as shown in FIG. 2. The actual rate of drug delivery is then the volumetric flow rate of the drug when flow tube 11 is open multiplied by the fraction of time flow is permitted during a cycle.

The calculated time sequence to accomplish the desired schedule of drug delivery has been stored in microprocessor 17. It includes a basic time interval or cycle that is continuously repeated. This calculated time sequence is illustrated in FIG. 2. The curves in FIG. 2 show the status of flow tube 11, open or closed, as a function of time.

Curve B in FIG. 2 shows one cycle, the shortest repeated increment in the calculated time sequence. The cycle begins at time $t_0$ and concludes at time $t_C$. Curve A in FIG. 2 illustrates the opening and closing of flow tube 11. When the cycle begins, pinch bar 14 has pinched flow tube 11 closed against pinch stop 12. At time $t_1$, pinch bar 11 is moved away from pinch stop 12 by means of cam operating motor 15 and cam 18, opening flow tube 11. Later, at time $t_2$, pinch bar 12 is moved back against pinch stop 14, closing flow tube 11. This pinching and unpinching action of flow tube 11 is controlled by microprocessor 17. At time $t_1$, microprocessor 17 sends a signal to cam operating motor 15 to rotate cam 18 180 degrees. This rotation of cam 18 causes pinch bar 14 to move away from pinch stop 12, opening flow tube 11, and initiating flow of the drug liquid through flow tube 11. At time $t_2$, microprocessor 17 sends another signal to cam operating motor 15, causing cam 18 to rotate another 180 degrees. This rotation of cam 18 causes pinch bar 14 to move against pinch stop 12, closing flow tube 11, and stopping flow of the drug liquid. Other methods of pinching and unpinching the flow tube as are known in the art, such as with a solenoid, or valve, may be used.

Curve C in FIG. 2 shows several cycles of the calculated time sequence during a period of time when the programmed drug delivery rate is constant. In this case, the time interval that flow is permitted each cycle ($t_1$–$t_2$) is the same. If a higher drug delivery rate is required, the fraction of time each cycle that flow tube 11 is open is increased. Similarly, if a lower drug delivery rate is required, the fraction of time flow tube 11 is open is decreased.

In an ideal world, factors affecting the actual rate of liquid flow down the flow tube such as the pressure in the reservoir, the viscosity of the drug fluid, and the inside diameter of the flow tube are constant. Thus the actual time that flow is permitted during the cycle would be directly calculated from the designed flow rate and the desired delivery rate as in equation (1) below. In an ideal world, this invention would not be needed.

In the real world, though, the reservoir pressure changes as the reservoir empties of the drug liquid. The drug liquid viscosity changes as the temperature of the liquid changes. The flow tube inside diameter also changes as temperature changes, and, if use of the system requires that the flow tube be changed, the inside diameter of the new tube is almost certainly different than that of the replaced tube. These and other changes can be sufficiently large to cause significant changes in the drug delivery rate. This is especially important in the case of insulin for the treatment of diabetes. It can also be true for Factor VIII for treating hemophiliacs, heparin for treating clotting disorders, theophyllin for treating asthma, and other drugs that have a very low therapeutic index.

For a given use of this drug delivery device, such as the delivery of insulin to treat diabetes, a certain drug delivery rate will be desired at a particular time. Based on the design of the system for this application, that is, the design pressure in the reservoir, the design viscosity of the drug solution, the length and inside diameter of the flow tube, and the separation of heating block and heat sensor, the time required for the drug beneath the heating block to travel to the heat sensor can be calculated. In actual use, though, the time measured will usually be slightly different than this nominal design time, and in some cases will be significantly different. If sufficiently different, the user can be alerted to the problem and replace the drug reservoir component. If the differences are small as they will be in most cases, the differences can be compensated for. If the measured time is shorter than the nominal time, this means that the rate of drug flow is higher. The fraction of the cycle that the flow tube is open can then be shortened by an appropriate amount such that the desired delivery is achieved. Similarly, if the measured time is longer than the nominal time, this means that the rate of drug flow is lower. The fraction of the cycle that the tube is open may then be lengthened by an appropriate amount such that the desired delivery is achieved.

To reduce or eliminate these real world variations, a metering means is incorporated into the drug delivery system, also shown in FIG. 1. As mentioned above, at the beginning of a cycle, flow tube 11 is closed. At this time, a small pulse of electrical power from microprocessor 17 is sent to heating block 13, causing the temperature of the small amount of drug liquid beneath heating block 13 to be raised a small amount (this small amount of heat will not raise the temperature enough to alter the potency of the drug). Flow tube 11 is then unpinched, allowing the drug liquid to flow along flow tube 11. The small amount of warmer drug liquid quickly moves to heat sensor block 16 where it is sensed. A signal is sent from heat sensor 16 to microprocessor 17 where the time that the warmer liquid passed through heat sensor 16 is recorded. In this way, the time required for the fluid to flow the distance from the heating block 13 to heat sensor block 16 is measured. This time will be defined as $T_M$.

In general, the volume of fluid Q delivered from a pressurized reservoir to an outlet through a flow tube, where F is the flow through the tube in time T is dictated by the equation:

$$Q = FT \qquad (1)$$

In a specific device, such as the drug delivery system of this invention, that is designed to provide a nominal or designed flow rate, $F_0$, the amount of fluid delivered or discharge Q in time T can be calculated using:

$$Q = F_0 T \qquad (2)$$

If two points on the flow tube are selected, say a first point where a heater is placed to inject a small amount of beat into the increment of fluid at that point, and a second point where a heat sensor is placed to detect the presence of the heated increment of fluid when it passes, and the time that it takes the heated increment of fluid to flow from the first point to the second point is defined as $T_0$, then the nominal discharge of fluid $Q_0$ from the flow tube in time $T_0$ can be calculated as:

$$Q_0 = F_0 T_0 \qquad (3)$$

Note that the physical significance of $Q_0$ is the volume of fluid in the flow tube between the first and second points described above.

Further, if the device is designed with means to first stop fluid flow in the tube, for example, with the tube pinching means described above; to second energize the heating element to heat the increment of fluid beneath it; to third activate the fluid stop means to start fluid flow; to fourth monitor the heat sensor until it measures a fluid temperature rise indicative of the passage of the heated fluid increment; and fifth measure the time required for the heated fluid increment to flow from the heating element to the heat sensor, then in the nominal or designed system, this time would be equal to $T_0$.

Finally, if the desired flow discharge from the nominal or designed drug delivery system during a delivery cycle as described above is $Q_D$, then the time $T_D$ that the fluid is permitted to flow before being stopped by fluid stop means can be calculated as:

$$T_D = \frac{Q_D}{F_0} = \frac{Q_D}{Q_0} T_0 \qquad (4)$$

Since $F_0 = \frac{Q_0}{T_0}$

Thus it can be easily seen that for the nominal or designed system, the determination of the time $T_D$ required to permit flow to achieve the desired drug delivery rate, which, of course, can be varied at the discretion of the user or his physician at any time by simply changing $Q_D$, is easily calculated from designed system parameters.

In use, the actual parameters that govern flow through the flow tube, such as the viscosity of the fluid, or the pressure in the drug reservoir, which is known to decrease as fluid is removed from the reservoir, both of which are dependent upon the temperature of the fluid, will rarely be the same as the design parameters. More importantly, when the reservoir component of the system is interchanged with a new, filled reservoir, the inside diameter of the flow tube in the new reservoir component will not be the exactly the same as the inside diameter of the tube in the reservoir component being replaced. Since flow in the flow tube varies with the fourth power of flow tube inside diameter, this is an especially important and perhaps dominant determinant of the actual flow, and hence the actual delivery of drug. Thus it is critical to provide a drug delivery system that automatically compensates for the unknown and unpredictable variations in these parameters in order to insure accurate drug delivery.

The provision of such a drug delivery system is the main object of this invention. In the following paragraphs, the method by which the invention automatically compensates for these variations of use and manufacture is described.

Case 1. Pressure Variations

When the pressure in the reservoir is higher than nominal, the fluid in the flow tube will flow at a higher rate. Conversely, when the pressure in the reservoir is lower than nominal, the fluid will flow at a lower rate. When the fluid flows at a higher rate, the time required to permit flow will be shorter than the nominal time, and when the fluid flows at a lower rate, the time required to permit flow will be longer than the nominal time. The key will be to determine a new time, $T_D{}'$ to permit fluid flow that provides for the desired drug delivery $Q_D$. Of course, it would be very easy in principle to include a pressure sensor on the reservoir component. However, since the reservoir component is intended to be disposable, this would add cost and complexity to a system component that needs to be as inexpensive as possible. The present invention avoids the need for such a pressure sensor. For ease of description, assume that the inside diameter of the flow tube is the nominal inside diameter such that the volume of fluid in the flow tube between the heater element and the heat sensor is $Q_0$. If the pressure and viscosity are also at the nominal value, then the flow rate will be $F_0$. According to the Poisieulle theory of laminar fluid flow in a tube (equation (9)), fluid flow rate varies linearly with a change in applied pressure. Thus, as the flow rate changes, the time that it takes the heated fluid increment under the heater element to move to the heat sensor will change to a new, measured value, $T_M$ in a linear fashion. Since the volume of the fluid, $Q_0$, between the heater element and the heat sensor is unchanged, the new flow rate can be calculated as:

$$F_M = \frac{Q_0}{T_M} \quad (5)$$

The new time, $T_D'$, that fluid flow should be permitted to deliver the desired dose of drug $Q_D$ to the patient under the new conditions of different pressure can be calculated as follows:

$$T_D' = \frac{Q_D}{F_M} = \frac{Q_D}{Q_0} T_M \quad (6)$$

Since $F_M = \frac{Q_0}{T_M}$

It can thus be seen that the only measurement needed to compensate for the change in pressure is the new time required for the heated increment of liquid to pass from the heater block to the sensor block, $T_M$. The desired delivery, $Q_D$ is specified since that is the delivery desired, and $Q_0$ is known from the system design.

Case 2. Viscosity Variations

The compensation of viscosity variations is essentially the same as for pressure variations. The only difference is that it is a temperature change that causes the viscosity of the drug solution to change—a viscosity change due to a drug solution formulation change is virtually impossible because of the product inspections required by the FDA. As temperature rises, the fluid becomes less viscous, and the flow rate increases. As temperature falls, the viscosity increase, and the flow rate decrease. As in the case of pressure change, for ease of description, assume that the volume of fluid in the flow tube is the nominal volume, $Q_0$. Again, according to the Poisieulle theory of laminar fluid flow (equation (9)), the flow rate varies linearly but inversely with viscosity. As in the case for pressure, a new time for the heated fluid increment to flow from heating element to the heat sensor, $T_M$ is measured. A new flow rate, $F_M$ is calculated the same way using equation (5). And, the new time, $T_D'$, required for fluid flow to deliver the desired dose of drug, $Q_D$, each cycle is calculated using equation (6).

Case 3. Combinations of Pressure and Viscosity Variation

The treatment is exactly the same as for either a pressure variation or a viscosity variation since the flow rate varies linearly with both pressure and viscosity. The system measures a new time, $T_M$, for a fluid increment to flow from the heating element to the heat sensor. A new flow rate, $F_M$, is calculated according to equation (5). And the new time, $T_D'$, required for fluid flow to deliver the desired dose of drug, $Q_D$, is calculated from equation (6).

Case 4. Variations in Flow Tube Diameter

Variations in flow tube diameter can be compensated for in a manner similar to the method used for variations in pressure and viscosity. However, because the flow rate varies with the fourth power of the diameter, according to the Poisieulle theory of laminar flow (equation (9)), the compensation formulas are different. For the purpose of clarity of description, again assume that the pressure in the reservoir, P, is nominal, as is the fluid viscosity, v. Further, let the total length of the flow tube equal L, and let the distance between the heating element and the beat sensor equal ½L. Let the diameter of a nominal flow tube be $D_1$, and the diameter of a new replacement flow tube be $D_2$. We then have the volume of the fluid in the nominal flow tube between the heating element and the heat sensor, $Q_0$, and the similar volume of the fluid in the new replacement flow tube, $Q_0'$, using straight geometry, as:

$$Q_0 = \frac{\pi L D_1^2}{8} \quad (7)$$

and $$Q_0' = \frac{\pi L D_2^2}{8} \quad (8)$$

By Poisieulle's theory of laminar flow in tubes, we have the following equations for liquid flow rate in the nominal tube, $F_0$, and for the liquid flow rate in the new replacement flow tube, $F_0'$:

$$F_0 = \frac{P D_1^4}{128 L v} \quad (9)$$

and $$F_0' = \frac{P D_2^4}{128 L v} \quad (10)$$

The nominal flow time between the heating element and heat sensor for a nominal flow tube, $T_0$, is given by the ratio of $Q_0$ and $F_0$, and can be derived as follows:

$$T_0 = \frac{16 \pi L^2}{P D_1^2} v \quad (11)$$

Similarly, the measured flow time between the heating element and the heat sensor in the new replacement flow tube, $T_M$ is given by the ration of $Q_0'$ and $F_0'$, and can be derived as follows:

$$T_M = \frac{16 \pi L^2}{P D_2^2} v \quad (12)$$

By dividing $T_0$ by $T_M$, that is, equation (11) by equation (12), the relationship between the nominal time, $T_0$ and the measured time for the new replacement flow tube, $T_M$ can be discovered. After some algebraic manipulation, the following relationship is found:

$$D_2^2 = \frac{T_0}{T_M} D_1^2 \quad (13)$$

Inserting equation (13) into equation (8) yields the following equation:

$$Q_0' = \frac{\pi L D_2^2}{8} = \frac{\pi L T_0 D_1^2}{8 T_M} \quad (14)$$

But $$Q_0 = \frac{\pi L D_1^2}{8} \quad (8)$$

Therefore $$Q_0' = \frac{T_o}{T_M} Q_0 \quad (15)$$

And since, from the basic flow equation $$F_0' = \frac{Q_0'}{T_M} \quad (16)$$

The new flow rate, $F_0'$ can be shown to be $$F_0' = \frac{T_0}{T_M^2} Q_0 \quad (17)$$

This is an important and unexpected result. The new flow rate for a new replacement tube can be expressed in terms of only nominal system parameters, $T_0$ and $Q_0$, and the new measured time $T_M$. It is not necessary to know any of the physical properties of the new replacement flow tube (except that its total length, which can be accurately cut during manufacture).

From these results, the time, $T_D$, required to permit fluid to flow down the flow tube to achieve the desired delivery of drug, $Q_D$, is $$T_D = \frac{Q_D}{F_0'} \quad (18)$$

And, finally, $$T_D = \frac{Q_D T_M^2}{Q_0 T_0} \quad (19)$$

This is the result needed for correcting for a new replacement flow tube. Despite not knowing the diameter of the replacement flow tube, the correct time to permit fluid flow down this new tube to compensate for any differences in its diameter can be determined by simply measuring the time required for the increment of heated fluid to move from the heating element to the heat sensor and using equation (19).

One issue remains, Since pressure and viscosity compensations are linear with $T_M$, and tube diameter compensations are quadratic with $T_M$, an important issue is to know when to make either a linear or quadratic compensation. In reality, this is easily done. When a new replacement flow tube is placed in the system this is the time to make the diameter compensation. At time of manufacture the pressure in a fresh reservoir can be set to nominal, and will remain at nominal over its shelf life. Temperature is easily and inexpensively measured (but even this may prove unnecessary since the product will be worn on the skin, and skin temperature is quite stable). Hence any differences between $T_0$ and $T_M$ at time of replacement of the disposable component will be due to a change in flow tube diameter. With this new flow tube in use, the nominal time $T_0$ can be reset to $T_M$ so that as the reservoir with the new flow tube is used, $T_M$ can be used as the new nominal flow time. As the system is used, the changes encountered will then only be due to viscosity and pressure changes that can be compensated using the linear correction.

In this manner, all of the expected variations that cause changes in fluid flow can be compensated, and accurate delivery of the desired dose of drug according to the stored schedule can be achieved.

Other embodiments to accomplish the invention may be known to those skilled in the art. For example, other methods of measuring the flow of the drug solution are known. One such method takes advantage of the fact that virtually all drugs solutions for administration to an animal are electrically conducting. If a magnetic field is placed perpendicular to the direction of drug flow, the induced flow of the ions in the drug solution results in a current flow in the direction of the magnetic field. Electrodes placed in appropriate positions can sense this current flow, which is directly proportional to actual volumetric flow rate. Alternatively, vanes or other mechanical devices can be placed in the flow path. When the liquid flows, the vanes will bend, resulting in a measure of flow rate.

Similarly, other methods of starting and stopping fluid flow are known. Valves may be placed in the flow path, and may be opened or closed as needed. Pressure on the medicament reservoir may be removed or replaced as needed.

While the above description of this automatic self-compensating liquid delivery system has been written in the context of a drug delivery system, the basic principles may be applicable elsewhere, for example, in an automobile carburetion system, in a paint dispensing system, in a gasoline station dispensing system, or any other system wherein an accurate and predictable liquid flow is required in a system where flow parameters may change.

The examples and embodiments described herein serve only to teach the invention and in no way serve to limit the scope of the invention. The scope is only limited by the following claims:

I claim:

1. A device for delivery of a liquid medicament to a subject comprising:
    a reservoir for containing the liquid medicament under pressure;
    a needle for penetrating the skin of the subject;
    a flow tube in fluid communication with the needle and the reservoir;
    a memory device for storing a schedule of delivery of the liquid medicament to a subject in terms of dose or dosing rate or both dose and dosing rate as a function of time;
    a meter for measuring properties of flow in the tube; and
    a valve for starting and stopping liquid flow in the flow tube in a periodic manner; wherein
        the time the valve is open or closed each period is adjusted to compensate for changes in system parameters as determined by measurements made by the meter so that the schedule of delivery is followed.

2. The device of claim 1 comprising two matable components; a first disposable component comprising the medicament containing reservoir, the needle, and the flow tube, and a second reusable component comprising the valve, the meter and the memory device.

3. The device of claim 1 or 2 wherein the liquid medicament is an insulin formulation.

4. The device of claim 1 or 2 wherein the liquid medicament is a narcotic analgesic formulation.

5. The device of claim 1 wherein the needle is at least one microneedle.

6. The device of claim 5 wherein the at least one microneedle has an outside diameter of less than 0.2 mm.

7. The device of claim 1 wherein the meter measures the time interval required for an increment of the liquid medicament to flow a prescribed distance along the flow tube.

8. The device of claim 1 wherein the device compensates for a change in pressure in the reservoir or a change in the viscosity of the liquid medicament, or both, by making a linear adjustment of the time that the valve is open or closed.

9. The device of claim 1 wherein the device compensates for a change of flow tube lumen dimensions by making a quadratic adjustment of the time that the valve is open or closed.

10. The device of claim 2 wherein the device compensates for a change in flow tube lumen dimensions by making a quadratic adjustment of the time that the valve is open or closed when the reusable component is first mated to a fresh disposable component.

11. The device of claim 2 wherein the disposable component includes a surface with an adhesive for adhering the disposable component to the skin of a subject.

12. The device of claim 1 wherein the meter measures the volumetric flow rate of the liquid medicament flowing in the flow tube.

13. The device of claim 1 wherein the meter measures the velocity of the liquid medicament flowing in the flow tube.

14. The device of claim 12 wherein the meter measures the volumetric flow rate by detecting a voltage generated by the flow the ions in the liquid medicament through a magnetic field.

15. A method of delivering a liquid medicament to a subject including the steps of
   a) providing a two component drug delivery device wherein the first component comprises a reservoir for containing a liquid medicament under pressure, a needle for penetrating the skin of the subject, and a flow tube connecting the reservoir and the needle, and wherein the second component is matable with the first component and comprises a valve for starting and stopping flow in the tube, a memory device for storing a delivery schedule for the liquid medicament in terms of dose or dosing rate or both dose and dosing rate as a function of time, and a meter for measuring properties of the flow of the liquid medicament along the flow tube,
   b) using the meter to make measurements of a property of flow of the liquid medicament, and
   c) using the measurements of a property of flow to deliver the liquid medicament according to the schedule by adjusting the time that the valve is open or closed to compensate for changes in system parameters.

16. The method of claim 15 wherein the system parameters being compensated for comprise at least one of reservoir pressure, medicament viscosity, and flow tube lumen dimensions.

17. The method of claim 15 wherein the system parameters being compensated for comprise reservoir pressure, medicament viscosity, and flow tube lumen dimensions.

18. The method of claim 16 wherein the adjustment of the time that the valve is open or closed to compensate for a change of flow tube lumen dimensions is a quadratic adjustment.

19. The method of claim 16 wherein the adjustment of the time that the valve is open or closed to compensate for changes in reservoir pressure and viscosity is a linear adjustment.

20. The device of claim 1, wherein the needle is at least one microneedle, wherein the device compensates for a change of flow tube lumen dimensions by making a quadratic adjustment of the time that the valve is open or closed, and wherein the meter measures the velocity of the liquid medicament flowing in the flow tube.

21. The device of claim 20, wherein the device includes an adhesive for adhering the device to the skin of a subject.

22. The device of claim 20, wherein the liquid medicament is an insulin formulation.

23. The device of claim 20, wherein the device comprises two matable components; a first disposable component comprising the medicament containing reservoir, the needle, and the flow tube, and a second reusable component comprising the valve, the meter and the memory device.

* * * * *